United States Patent [19]

Muhlbauer

[11] Patent Number: 4,632,243
[45] Date of Patent: * Dec. 30, 1986

[54] BATCH PACK FOR SILVER FILINGS FOR THE PREPARATION OF DENTAL AMALGAM

[76] Inventor: Ernst Muhlbauer, Dorpfeldstieg 3, 2000 Hamburg 52, Fed. Rep. of Germany

[*] Notice: The portion of the term of this patent subsequent to Aug. 27, 2002 has been disclaimed.

[21] Appl. No.: 743,826

[22] Filed: Jun. 12, 1985

Related U.S. Application Data

[63] Continuation-in-part of Ser. No. 557,472, Dec. 2, 1983, Pat. No. 4,537,303.

[30] Foreign Application Priority Data

Feb. 4, 1983 [DE] Fed. Rep. of Germany ....... 3303838
Feb. 22, 1985 [DE] Fed. Rep. of Germany ....... 3506345

[51] Int. Cl.$^4$ ............................................. B65D 25/08
[52] U.S. Cl. .................................. 206/219; 206/220; 206/63.5
[58] Field of Search ....................... 206/219, 220, 63.5

[56] References Cited

U.S. PATENT DOCUMENTS

| | | | |
|---|---|---|---|
| 4,182,447 | 1/1980 | Kay | 206/220 |
| 4,291,799 | 9/1981 | Bower, Jr. | 206/219 |
| 4,306,651 | 12/1981 | Muhlbauer | 206/220 |
| 4,312,473 | 1/1982 | Hoeller | 206/219 |

Primary Examiner—Joseph Man-Fu Moy
Attorney, Agent, or Firm—Prutzman, Kalb, Chilton & Alix

[57] ABSTRACT

A batch pack for silver filings is employed in the preparation of dental amalgam in a laboratory mixing apparatus. The batch pack comprises a foil bag which can be destroyed by the mixing vibration and a briquette or tablet of silver filings. The density of the briquette of silver filings is not more than about 8 gram per cubic centimeters or a pore volume of about 20 percent of the volume of the briquette.

12 Claims, 14 Drawing Figures

BATCH PACK FOR SILVER FILINGS FOR THE PREPARATION OF DENTAL AMALGAM

CROSS-REFERENCE TO RELATED APPLICATION

This application is a continuation-in-part of U.S. Application Ser. No. 557,472 filed Dec. 2, 1983 now U.S. Pat. No. 4,537,303.

BACKGROUND AND SUMMARY OF THE INVENTION

This invention relates to a batch pack for silver filings for the preparation of a dental amalgam in a laboratory mixing apparatus. More particularly, this invention relates to a foil bag which is inserted in a mixing chamber and exposed to mixing vibration for releasing the contents of the foil bag under the action of the mixing vibration.

In U.S. Pat. No. 4,306,651 issued to the present applicant which patent disclosure is incorporated herein by reference, a multi-component capsule for dental purposes is shown wherein one component is freely contained in the mixing chamber of the capsule and the other component is contained in the foil bag and thereby separated from the one component until the foil bag is destroyed by the mixing vibration. Naturally, it is sufficient to enclose merely one component in a bag so as to insure chemical separation during the storage period. The use of a multi-component capsule for storage and for a single mixing operation involves a certain expenditure which can be avoided where the dentist places silver powder as well as, by means of a dosing apparatus, a corresponding quantity of mercury into a mixing capsule for multiple use, closes the capsule and subsequently mixes the components in a vibration apparatus. While this method is less expensive, inexact dosages may result more readily than with a mechanical pre-dosing, and the physician is exposed to the immediate influence of the mercury.

The present invention concerns the problem of combining the simplicity of the method as known from the use of disposable capsules with the low expenditure involved in the repeated use of the capsule. A solution according to the invention resides in the fact that the powdery component is also enclosed in a separate foil bag which is exposed to vibration and opens under the action of the mixing vibration, with the foil bag consisting of a material having a specific gravity several times lower than that of the powdery component.

The enclosure of both components in respective foil bags permits their optional use, irrespective of whether they are supplied in a disposable capsule or whether they will be inserted by the dentist into a mixing capsule to be used if necessary several times. Furthermore, the enclosure of both components permits an easy and simple dosing by inserting in each case such a number of foil bags containing the components into a mixing capsule in accordance with the desired amalgam amount.

Powder would not be expected to liberate itself sufficiently completely from a foil bag which opens under mixing vibration since such characteristics cannot be expected even of the liquid component under certain conditions. For example, there is the possibility that mercury will not be distributed completely from a sealed metal foil bag as disclosed in U.S. Pat. No. 4,182,447. If the complete emptying of the foil bag appears not to be insured even with liquids under certain conditions, then this would much less be expected as regards the storage of a powder in a foil bag. It is more surprising that the complete discharge of the powdery component is achieved if in accordance with the present invention the specific gravity of the bag material is several times lower than that of the powder. It may be assumed that this effect is due to the fact that in accordance with the physical law of force equals mass times acceleration, the forces exerted by the various vibration accelerations and the substances contained in the capsule are considerably smaller in relation to the specifically lighter bag material than in relation to the powder particles so that the latter is separated from each other by the very different forces acting on them. It may also be of importance in this connection that under vibration conditions the powder does not behave as solid material but behaves very similar to a liquid. This latter characteristic is due to the fact that powder particles get into a relative motion with respect to each other whereby air layers are enclosed between them which terminate the solid connection and put the powder as a whole into a so-called fluidized state, which state is known as being used in another technical field, namely that of the mechanical conveying and handling of powdery material.

It can easily be determined by experiments by how many times the specific gravity of the powder must be greater than that of the bag material. There is to be achieved a density ratio, relative to the solid powder material, of at least 5 and preferably of more than 8.

The invention relates furthermore to a mixing capsule for carrying out the stated method of the vibration mixing of several components contained therein particularly for dental purposes. The mixing capsule contains in a mixing chamber a liquid component tightly enclosed in a foil bag for releasing said component under the action of mixing vibration in a powdery component. The powdery component is contained in a separate foil bag which opens under the action of the mixing vibration with the foil bag consisting of a material having a specific gravity several times less than that of the powdery component by a factor of at least 5 and preferably more than 8.

Finally, this invention relates to a portion package for silver powder or the like powdery dental material intended for a vibration mixing in a dental mixing capsule. In the package, the powder is enclosed in a foil bag, the material of which is specifically several times lighter than the powder and the strength of which is predetermined such that it opens under the action of the mixing vibration in the mixing chamber of the dental mixing capsule.

The enclosure of the powder, particularly the silver powder or the silver filings, in a foil bag has a great advantage that the portion size can be pre-determined with great exactness. Dental amalgam is prepared by the dentist from silver filings and mercury to obtain a more accurate dosage. It is known to prepare batch packs of the two components, which batch packs are together introduced into a mixing capsule which is exposed in a mixing apparatus to a mixing vibration of, for example, 300 Hz. Known batch units for the silver filings consists of pellet-shaped pressings which are supplied loose in a relatively large number in a suitable packaging container. To prevent an excessive loss of their weight due to mutual attrition and to enable them to be handled without a risk of breakage, the pellet-shaped tablets are compressed to a high density which approaches the density of the solid metal to within a few percent. Nevertheless, the formed tablets can suffer an undesirably large weight loss due to attrition, particularly if the tablets are inexpertly handled and remain for a long time in the common container. The tablets also have the disadvantage that under the action of vibration in the mixing capsule the tablets disintegrate sufficiently into reactive powder only in the presence of a pestle.

It is also known to store such tablets in a foil bag such as disclosed in European Published Application 83 106110 wherein at least the attrition loss is eliminated but the need for a pestle is not avoided. Moreover, it is known to introduce the silver filings in the form of a powder into the foil bag. This latter configuration has the advantage that the silver filings are available immediately in the reactive form. Nevertheless, a pestle is required in most cases, namely in order to accomplish destruction of the foil bag. Even though the foil bag can be made so thin that even without a pestle it tears under the acceleration forces exerted by the powder and the adjacent mercury during the mixing vibration, the use of somewhat thicker foil is frequently desirable in order to provide greater safety for good separation of the components and against the formation of relatively small foil residues which might make clean removal of the amalgam more difficult.

It is therefore an object of the present invention to provide a batch pack for silver filings for the preparation of dental amalgam in a laboratory mixing apparatus which is easier to handle. In accordance with the present invention the silver filings are pressed into a briquette for enclosure within the foil package. The density of the briquette is not more than approximately 8 gram/cm$^3$ and preferably not more than 7.5 gram/cm$^3$. The density of the pore volume of the briquette is at least approximately 20 percent.

According to a further feature of the present invention, portion packages of the dental material components to be used together can be connected to each other. This presents not only the advantage that the use is simplified since in each case only one portion of the package with both components needs to be inserted in the mixing capsule but also the portioning becomes more reliable since no mistakes can occur in the coordination of component amounts suited to each other. Additionally, several portion packages can be inserted in the mixing capsule at a time, such as for a large tooth filling wherein there is required an amalgam amount greater than that provided by one portion package.

The connection of the two individual portion packages to a common portion package can be achieved in a simple way, e.g., by adhesion bonding. According to another feature of the present invention, the connection between the individual portion packages is obtained in that at least one foil is involved in the formation of both portion packages. Preferably, even both portion packages are formed integrally by a pair of foils, which are welded together in forming two separate portion pockets.

According to a further embodiment of the invention, two cover foils are welded together with a central foil to form two portion pockets situated on both sides of the central foil.

The destruction of the foil bag containing the liquid component is facilitated by the powdery component being packed in a foil bag combined as a unit with the liquid bag, since the entire powder material substantially simultaneously exerts impact on the liquid bag and thus a stronger effect thereon than simply a powder distributed in the entire space.

There may be provided devices which improve the opening of the foils under the action of the mixing vibration and/or the mixing effect, for example a pestle, which may also be contained in the portion package, or edges or prongs projecting inwards from the wall of the mixing chamber.

If a capsule is to be used repeatedly for the preparation of a dental amalgam, the capsule must be cleaned between individual applications or at least from time to time. Furthermore, the capsule has to be considered a disadvantage in that the prepared mixture must be taken out of the capsule in a relatively complicated way, and in which respect also the remainders of the consumed packaged, likewise contained in the capsule, can be inconvenient. Such a disadvantage can be avoided in accordance with the present invention in that the package foil, destructible by the action of the mixing vibration, together with the portion chamber separated therefrom and including the dental material components, is enclosed by a package casing not destructible by the action of the mixing vibration.

After the mixing process, the mixed material is now contained in the free form within the mixing chamber of the mixing capsule but is still enclosed by the foil bag, wherein merely the inner separating foil has been destroyed. One can therefore simply take the closed portion package out of the mixing capsule, tear the portion package open and take out the mixture by a spatula or squeeze the mixture out between two fingers. Thus, the removal of the mixture is substantially simplified and is achieved without special measures in a fashion wherein the mixture remains hygenic.

The arrangement of the package foil destructible by the mixing vibration with respect to the non-destructible packaging casing can be different. In one advantageous embodiment there are provided for example two foil bags, one of which freely encloses as a covering foil bag the first dental component as well as the destructible foil bag containing the second dental material component. In accordance with another expedient embodiment, it is provided that two foils, together forming the covering foil bag, are welded together on both sides of the destructible foil either to the latter or to each other.

After mixing, the outer package casing which is not destructible by the mixing vibration forms a container for the mixed dental material. In order that the container can be handled more easily, it can be formed according to the invention as a semi-flexible cup-like package portion. The term semi-flexible means that the container retains the cup-shape in a more or less deformed state even if it is held between the fingers in order to be emptied. Its cup-shape facilitates the removal of the mixed material.

Additionally, it may be provided according to the present invention that the package casing is provided with an opening device. An opening device is understood to mean those elements or formations which enable or facilitate the opening process. This includes, for example, gripping lugs projecting outwards from the portions forming the actual package casings so as to allow, for the purpose of opening, a gripping thereof in the exertion of a force. Furthermore, this includes ideal tearing points in notches in the welding edge in which the opening tear may be started.

The portion package according to the present invention can enclose the dental material components without a substantial empty space so that the mixing forces created upon the impact of the portion package during the mixing vibration at the ends of the mixing capsule will be transferred, without being damped, onto the dental material components to be mixed. This applies particularly of a flexible material as used for the non-destructible package casing, which completely transmits the forces to the dental material. Instead of this, it may, however, also be provided that the portion package includes a certain empty space permitting a certain vortexing. This applies particularly if the package casing consists wholly or partially of a semi-flexible or stiffer material.

It may also be expedient that the portion package contains a pestle, i.e., a body of for instance glass, ceramics, synthetic material, which due to its movement within the portion package, caused by the mixing vibration, assists in the mixing of the components. It is not necessary that the two component bags are inserted in the mixing capsule only by the dentist and immediately prior to use, but the invention rather presents also the advantage that the filling of the capsule becomes independent of the dosing and encasing of the components. Finally, there is achieved an advantage wherein it is not necessary to tightly close the capsule, even if the latter is intended for long term storage, such that the components in their bag packages can be sufficiently sealed against atmospheric influences and evaporation of poisonous gases into the atmosphere is prevented.

The foil packages may be provided with imprints, i.e., with statements required under the drug law, such as the name of the manufacturer, weight, durability, date of filing, specification of the materials, etc. The individual foil packages can be lined up as double packages or individually within a strip of similar packages and can be separable from each other and, if necessary, from the strip section provided with the information by perforation or pre-determined breaking points, respectively.

The invention presents considerable price advantages over the known disposable capsules, which mostly have to be additionally prepared for mixture by turning, pressing, or screwing. The encasing of the amalgam powder in foil bags can also be advantageous over the processing in the form of tablets since the latter first have to be compressed which involves cost. Moreover, it can be disadvantageous for some amalgam powders to be compressed tablets. Finally, the abrasion of the tablets may lead to differences in weight. Compared with the use of automatic mixers, the invention involves the advantages of a greater exactness, the amalgams of any kind can be used, so that no maintenance of the apparati is required and so that the dentist is not exposed to mercury vapor.

The portion package of the components to be mixed can be inserted in the mixing capsule at any point of the chain between production, storage and use.

In the context of the invention, both the mixing capsule and the vibration mixers used for dental purposes can be considered to be known. Mixing capsules are elongated containers closed by a removable lid having a length in the order of 3 cm and a diameter on the order of 1 cm. The mixers are formed so that the mixing capsules inserted therein can be reciprocated in their longitudinal direction at a frequency of 300 Hz so that the material contained in the interior of the capsule (the mixing chamber) is flung to and fro between the end walls of the mixing chamber. The volume of the material amounts to only a very small portion of the volume of the mixing chamber. Typical amalgam portions as they are prepared by the dentist in one mixing operation lie between 0.5 grams and 1 gram.

With respect to foil materials, they are particularly suitable synthetic materials, e.g., a polyethelyne foil of thickness on the order of magnitude of 0.05 mm.

DESCRIPTION OF THE PREFERRED EMBODIMENTS

Figure 1:
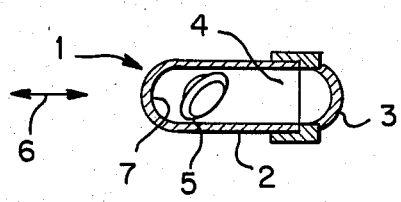
FIG. 1 is a longitudinal section through a mixing capsule in about normal size.

The mixing capsule 1 consists of a container portion 2 and a removable lid 3 which is fittingly arranged thereon and can, if necessary, be closed again. The elements together enclose the mixing chamber 4 in which a portion package 5 is disposed which comprises respective portion pockets for matching amounts of mercury and silver powder or filings. By vibration of the capsule in a mixer (not illustrated) in the direction of the arrow 6, the portion package 5 is alternately caused to vigorously impact on both front surfaces of the mixing chamber 4. The packing casing is torn up during the impact to release the contents so that the mixing of the components can take place. In order to facilitate the tearing up of the packing casing and if necessary also the mixing process, one front surface comprises, at 7, a pointed projection extending into the mixing chamber.

Figure 2:
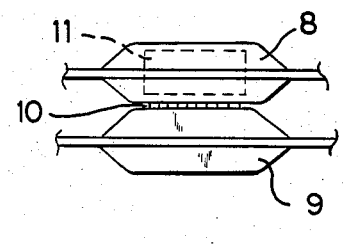
FIG. 2 is a portion package with two individual portion packages connected by gluing.

According to FIG. 2, the portion package consists of two individual packages 8, 9, for silver and mercury, respectively, which packages are connected to each other by adhesion bonding 10. The silver powder or the silver filings can be contained therein in the form of powder or also as shown at 11 by dotted lines, in the form of a tablet or a briquette. The briquette of silver filings is compressed to have a density of not more than approximately 8 g/cm$^3$ and preferably not more than 7.5 g/cm$^3$. This latter relationship corresponds to a difference, relative to the density of the solid metal form of silver of 17-22 percent pore volume contained in the briquette. The density can therefore also be defined by the relationship wherein the pore volume of the briquette is at least approximately 20 percent.

Surprisingly, the lower density of the briquette form has the consequence that the use of a pestle becomes unnecessary. On the one hand, the compressive strength of the briquette is sufficient for it to act as a unitary impact body when the point is the destruction of the foil surrounding. On the other hand, the compressive strength is so low that the acceleration forces which arise during the mixing vibration are sufficient for disintegrating the briquette into a reactive powder. The compressive strength (measured in the direction of the diameter of a specimen pellet of 2 mm height and a 6 mm diameter) is not greater than about 50 newtons. Typically the compressive strength is on the order of magnitude of approximately 40 newtons. By contrast, the compressive strength of the known tablets is at least about twice as large.

While low density of the briquettes can have the result that on mechanical handing of the briquettes, the briquettes suffer weight losses due to attrition or breakage, the latter can easily be avoided by an appropriate gentle treatment of the briquettes during the handling in the factory before packaging. It is, of course, immaterial after the briquettes have been enclosed in the foil bag.

In one example of a briquette of silver filings in accordance with the present invention, the commercially available silver filings have the following composition:

SILVER—68% BY WEIGHT
TIN—26% BY WEIGHT
COPPER AND ZINC—REMAINDER

The foregoing filings are compressed to form briquettes or tablets which are defined by two mutually parallel surfaces and cylindrical surfaces perpendicular thereto. The diameter is 6 mm, the height is 2 or 3 mm and the weight is 400 or 600 mg, respectively. A compressive force of about 10 KN is applied to compress the filings into the foregoing briquettes. The compressive force results in a density of 7.1 g/cm$^3$. The compressive strength between the two plates acting diametrically on the cylinder surface is 40 newtons. The briquettes or tablets formed in accordance with the invention were sealed in foil bags of Surlyn film having a film thickness of 0.05 to 0.07 mm.

By contrast, known tablets or briquettes of the same weight as the foregoing examples have a height of 1.5 or 2.5 mm and are compressed with a pressure force of about 20 KN and have a compressive strength of around 100 N.

A batch pack incorporating the foregoing examples of briquettes of silver filings together with a corresponding mercury batch pack was subject, in a customary elongate mixing capsule in a commercially available laboratory mixing apparatus to a vibration of 300 Hz in the longitudinal direction of the capsule. The foil bag surrounding the briquette was opened by vibration without being torn into small pieces. The briquette disintegrated into powder and was perfectly mixed with the mercury.

The batch pack as described above can even from the factory be marketed together with corresponding mercury batches or mercury batch packs in mixing capsules which are then used as disposable mixing capsules. Instead, it is also possible to sell the batch pack according to the invention individually, namely in the form of a multiplicity of such batch packs in a common container, for example, in the way hitherto conventional for individual briquettes of silver filings. The batch pack together with the mercury is then introduced by the dentist into a mixing capsule which can be used several times.

Figure 3:
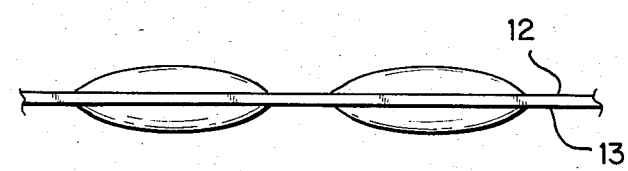
FIG. 3 is a side elevation view of a portion package connected to form one piece.
Figure 4:
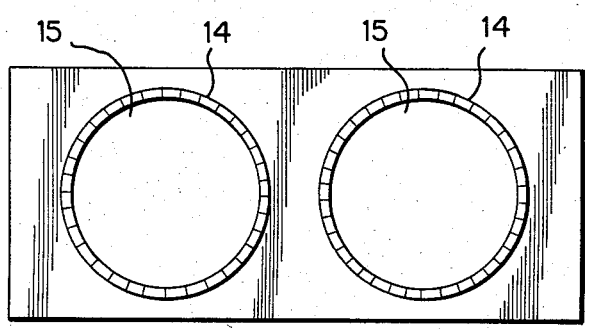
FIG. 4 is a top plan view of a portion package connected to form one piece.

The second embodiment of the portion package according to FIGS. 3, 4 consists of two foils 12, 13 which are welded together in closed circles 14 to form tight portion pockets 15 for respectively receiving the silver powder or filings and the mercury or other dental materials.

Figure 5:
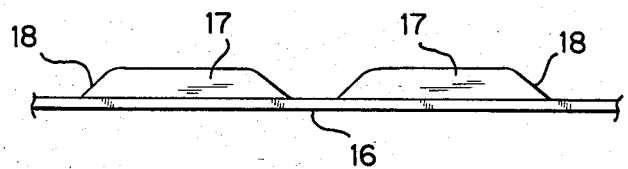
FIG. 5 is a third embodiment of the present invention.

In the third embodiment according to FIG. 5, only one foil 16 is formed to be continuous, whereas the portion pockets 17 thereon are formed by individually cut-out foil pieces 18 and a welding corresponding to FIG. 4.

Figure 6:
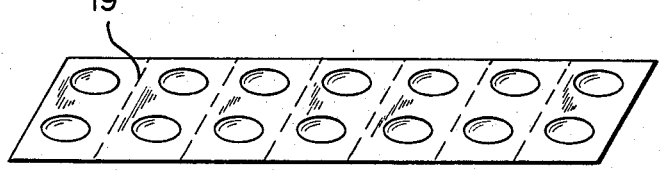
FIG. 6 is a package strip comprising several double portion packages separable from each other.

The portion packages according to FIGS. 3 and 5 can be kept in stock in the form of packaged strips according to FIG. 6, wherein the portion packages, each of which consists of two individual packages for the two components, can be easily separated from each other by means of a perforation 19.

Figure 7:
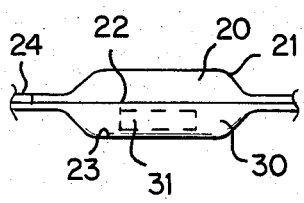
FIG. 7 is a fourth embodiment of the present invention on an enlarged scale.

In the fourth embodiment according to FIG. 7, two covering foils 21, 23 are circumferentially tightly welded in the area 24 to a central foil 22 to form two portion pockets 20, 30. At least three of the foils are designed such that they become destroyed under the action of the mixing vibration and will release the contents. In FIG. 7, it is moreover shown that the portion package can comprise a pestle 31, for instance, in an inert plastic or glass piece in one of the portion pockets.

Figure 8:
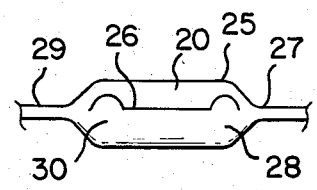
FIG. 8 is a fifth embodiment of the portion package of the present invention on an enlarged scale.

A fifth embodiment, similar to the embodiment according to FIG. 7, is shown in FIG. 8, with the difference that the central foil 26 is welded separately to the covering foil 25 at 27, while the other covering foil 28 is welded to the covering foil 25 at a distance from the welding seam 27 at 29. All welding seams are effected circumferentially so that the pockets 20, 30 are completely closed. The spacing of the welding seams 27, 29 presents the advantage that they can be effected separately as to time and space.

Of course, the portion packages according to FIG. 2 or 7 or 8 can also be combined in a plurality thereof to package strips according to FIG. 6 so as to be separable from each other.

It is, of course, not necessary that in each portion package all foils serving for its formation are destructible under the action of the mixing vibration, but it is sufficient if in each case one foil used in the formation of each portion package is destructible. In many cases, it is also sufficient if only one of these foils has a specific gravity several times lower than that of the powder component, even though expediently both foils used for forming the portion pockets provided for receiving the powder should comply with this requirement.

Figure 9:
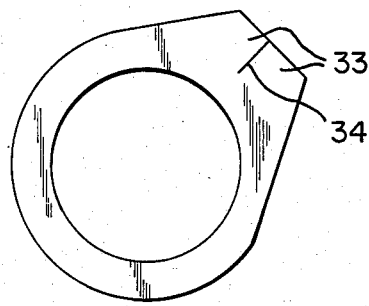
FIG. 9 is a top plan view of the sixth embodiment of the portion package.
Figure 10:
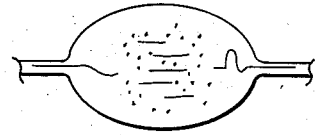
FIG. 10 is a section view corresponding to FIG. 7 through the sixth embodiment of the package after mixture thereof.

According to a sixth embodiment, which may be described likewise by reference to FIGS. 7 and 8, the covering foils 21 and 23 or 25 and 28, respectively together form a package casing not destructible by the mixing vibration while the central foil separating the portion pockets 20, 30 is made such that it tears under the action of the mixing vibration, whereby, in accordance with FIG. 10, the two components can together be mixed by the vibration. The welding seam can form, according to FIG. 9, two adjacent, outwardly projecting lugs 33, between which a slot or a notch is provided. By pulling the lugs 33 in different directions, it is possible, starting from the notch 34 to tear up the bag after mixture in order to enable the removal of the contents.

Figure 11:
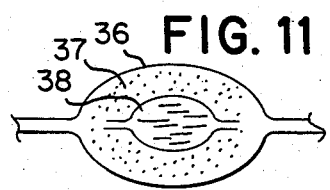
FIG. 11 is a seventh embodiment of the present invention with two bags, one disposed within the other.
Figure 12:
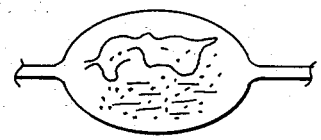
FIG. 12 illustrates the embodiment of FIG. 6 after completion of a mixing operation thereof.

In the seventh embodiment according to FIGS. 11 and 12, there is, apart from the silver powder 37 freely housed in the package casing 36 consisting of two foils welded together and not being destructible by mixing vibration, also a second package bag 38, which consists of the foil destructible by the mixing vibration and containing the mercury. During the mixing vibration, the bag according to FIG. 12 is destroyed so that the two components come into contact.

Figure 13:
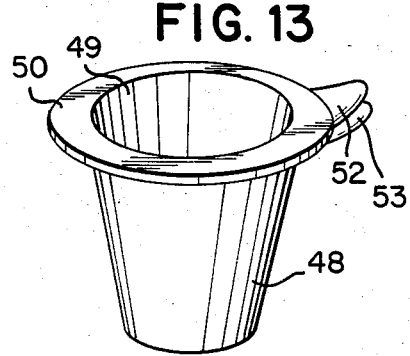
FIG. 13 is a perspective illustration of the eighth embodiment of the present invention.
Figure 14:
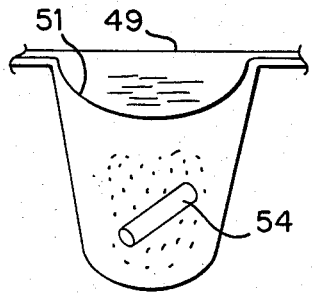
FIG. 14 is a sectional view of an eighth embodiment of the present invention.

The foils which form the package casing in FIGS. 7-12 can be soft so that they do not tend to assume a specific configuration. After opening, the contents may be squeezed out of the packages. However, it is also possible instead of the latter that one of the two encasing foils is more rigid so as to form, after separation of the other encasing foil and, if necessary, of the separating foil, a dish or cup-shaped container, of which the mixed material can more easily be removed. In that case, the opening devices are expediently formed such that it is possible to pull off one encasing foil like a lid, along the corresponding weaker welding seam, from the edge of the other encasing foil which is formed as a dish or cup. The embodiment according to FIGS. 13 and 14 likewise follows the latter principle, wherein the markedly cup-shaped portion 48 of the package encasing is relatively rigid, while the covering foil 49 which is welded on to the rim of the cup portion 48 along the welding seam 50 and enclosing the separating foil 51, can be flat. The covering foil and the cup portion 48 are provided at their rim with lug-like projections 52, 53, which can be gripped so as to enable the pulling off of the covering foil from the rim of the cup portion 48. In this connection, the arrangement can be such that the separating foil 51 (in deviation from the illustration) is connected exclusively to the covering foil 49 or that the common welding seam of all three foils is weakest between the separating foil 51 and the rim of the cup portion 48 so that, when pulling off the covering foil 49 there will be simultaneously separated also the remainders of the separating foil from the cup portion 48.

The cup portion 48 can be made rather large with respect to the volume of the components to be mixed, so that there remains a gas filled space, in which the components to be mixed can be hurled around with the mixing-improved effect when the package hits upon the ends of the mixing capsule. For improving the mixing effect, a pestle 54 can be additionally inserted. If reference is made in the claims to the cup-shape, such reference should include also similar forms such as the dish shape in accordance with FIG. 7.

In the sixth to eighth embodiments, the foil which is destructable by the mixing vibration has expediently likewise a specific gravity several times lower than that of the powdery dental material, although these embodiments can be used also with materials having a specific gravity in the same order or even lower than that of the foil, for instance, with the components or fillers for synthetic resinous dental materials.

While a preferred embodiment of the foregoing invention has been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. A dental vibration mixing capsule for vibration mixing a dental amalgam comprising:
   a capsule having a fully closed mixing chamber and adapted for vibratory mixing motion;
   a first package portion having a foil pocket containing a predetermined amount of powdery dental component comprising a briquette of silver filings compressed to a density of not more than approximately 8 g/cm$^3$, said foil pocket being comprised of a foil material adapted to rupture and discharge said predetermined amount of powdery dental component in said mixing chamber during vibration mixing and the foil having a specific gravity at least five time less than the specific gravity of the powdery dental component, said first package portion being disposed in said mixing chamber; and
   a second package portion having a foil pocket containing a predetermined amount of liquid dental component coordinated to said predetermined amount of powdery component to form a dental amalgam of fixed predetermined proportions of said liquid dental component and powdery dental component, said foil pocket being comprised of foil material adapted to rupture and discharge said predetermined amount of the liquid dental component in said mixing chamber during vibration mixing, said second package portion being disposed in said mixing chamber whereby said predetermined portion of the powdery dental component is separated from said liquid dental component during storage and said predetermined portion of the powdery dental component admixes with said predetermined portion of the liquid dental component to form an amalgam of said fixed predetermined proportions of said liquid dental component and said powdery dental component during mixing vibration of said capsule housing.

2. A portion package for a powdery dental component of a dental amalgam of said powdery dental component and a liquid dental component for vibration mixing of said components in a dental mixing capsule comprising:
   a predetermined amount of the said powdery dental component for forming a dental amalgam of fixed predetermined proportions of said powdery dental component and the said liquid dental component, said powdery dental component comprising a briquette of silver filings having a density of not more than approximately 8 g/cm$^3$; and
   a foil bag including said powdery dental component, said foil bag being of sufficient strength to rupture and thereby discharge said predetermined amount of said powdery dental component during vibration mixing in a dental mixing capsule and being comprised of a material having a specific gravity at least five time less than the specific gravity of said powdery component whereby said foil bag ruptures under the vibratory mixing in a dental mixing capsule and discharges said predetermined amount of said powdery dental component.

3. A dental material package assembly of dental material components for vibration mixing in a dental mixing capsule comprising:
   a first package portion enclosing a predetermined amount of a first powdery dental component comprising a briquette of silver filings having a density of not more than approximately 8 g/cm$^3$, the first package portion being formed by a foil material having a specific gravity at least five time less than the specific gravity of said first powdery component;

a second package portion of foil material enclosing a predetermined amount of a second liquid dental component coordinated to said predetermined amount of said first powdery dental component for forming a dental amalgam of fixed predetermined proportions of liquid dental component and said powdery dental component, said second package portion being connected to said first package portion; and said first and second package portions being formed at least in part by a rupturable foil adapted to rupture by mixing vibration in a mixing capsule to release said predetermined amounts of said powdery dental component and said liquid dental component to form a dental amalgam of said fixed predetermined proportions of said liquid dental component and said powdery dental component during vibration mixing of the mixing capsule.

4. The dental vibration mixing capsule of claim 1 wherein said briquette of silver filings has a density of not more than 7.5 g/cm$^3$.

5. The dental vibration mixing capsule of claim 1 wherein the briquette of silver filings has a pore volume of at least approximately 20 percent of the volume of the briquette.

6. The dental vibration mixing capsule of claim 1 wherein the compressive strength of the briquette of silver filings is not greater than approximately 40 Newtons.

7. The portion package of claim 2 wherein said briquette of silver filings has a density of not more than 7.5 g/cm$^3$.

8. The portion package of claim 2 wherein the briquette of silver filings has a pore volume of at least approximately 20 percent of the volume of the briquette.

9. The portion package of claim 2 wherein the compressive strength of the briquette of silver filings is not greater than approximately 40 Newtons.

10. The dental material package assembly of claim 3 wherein said briquette of silver filings has a density of not more than 7.5 g/cm$^3$.

11. The dental vibration mixing capsule of claim 3 wherein the briquette of silver filings has a pore volume of at least approximately 20 percent of the volume of the briquette.

12. The dental material package assembly of claim 3 wherein the compressive strength of the briquette of silver filings is not greater than approximately 40 Newtons.

* * * * *